(12) United States Patent
Burbank et al.

(10) Patent No.: US 6,497,706 B1
(45) Date of Patent: Dec. 24, 2002

(54) BIOPSY DEVICE AND METHOD OF USE

(75) Inventors: Fred H. Burbank, Laguna Niguel; Frank Louw, Carlsbad; Paul Lubock, Laguna Niguel, all of CA (US)

(73) Assignee: SenoRx, Inc., Aliso Viejo, CA (US)

( * ) Notice: Subject to any disclaimer, the term of this patent is extended or adjusted under 35 U.S.C. 154(b) by 28 days.

(21) Appl. No.: 09/717,176

(22) Filed: Nov. 16, 2000

Related U.S. Application Data (63) Continuation of application No. 09/477,255, filed on Jan. 4, 2000, and a continuation-in-part of application No. 09/159,467, filed on Sep. 23, 1998, now Pat. No. 6,261,241, which is a continuation-in-part of application No. 09/057,303, filed on Apr. 8, 1998, now Pat. No. 6,331,166.
(60) Provisional application No. 60/076,973, filed on Mar. 3, 1998.

(51) Int. Cl.⁷ .......................... A61B 18/18; A61B 10/00
(52) U.S. Cl. ........................ 606/45; 606/49; 606/50; 600/565
(58) Field of Search .................. 606/41, 45, 48, 606/49, 50, 167, 170; 600/562–567

(56) References Cited

U.S. PATENT DOCUMENTS

| | | | |
|---|---|---|---|
| 2,032,860 A | 3/1936 | Wappler et al. | |
| 2,192,270 A | 3/1940 | McGowan | |
| 3,341,417 A | 9/1967 | Sinaiko | 606/130 |
| 3,805,791 A | 4/1974 | Seuberth et al. | |
| 3,818,894 A | 6/1974 | Wichterle et al. | |
| 3,823,212 A | 7/1974 | Chvapil | |
| 3,955,578 A | 5/1976 | Chamness et al. | |
| 4,007,732 A | 2/1977 | Kvavle et al. | |
| 4,172,449 A | 10/1979 | LeRoy et al. | 600/431 |
| 4,197,846 A | 4/1980 | Bucalo | |
| 4,202,338 A | 5/1980 | Bitrolf | |
| 4,243,048 A | 1/1981 | Griffin | 600/567 |

(List continued on next page.)

FOREIGN PATENT DOCUMENTS

| | | |
|---|---|---|
| DE | 12 25 813 | 9/1966 |
| DE | 19528440 A1 | 8/1995 |
| EP | 146699 | 9/1984 |
| EP | 0255123 | 2/1988 |
| EP | 0292936 | 11/1988 |
| EP | 0472368 A2 | 8/1991 |
| EP | 0481685 A1 | 10/1991 |
| EP | 0667126 A1 | 8/1995 |
| EP | 0 919 190 A | 6/1999 |
| EP | 0 983 749 | 3/2000 |

(List continued on next page.)

OTHER PUBLICATIONS

J. S. Armstrong et al. "Differential marking of excision planes in screened breast lesions by organically coloured gelantins [see comments]" *Journal of Clininical Pathology* (Jul. 1990) 43(7):604–7, XP000971447 abstract; tables 1 and 2.

(List continued on next page.)

*Primary Examiner*—Roy D. Gibson
(74) *Attorney, Agent, or Firm*—Coudert Brothers LLP (57) ABSTRACT

A device and method of using the device to access a desired tissue site within a patient's body and separating a tissue specimen from the tissue site suitable for evaluation. The device includes a probe member having an arcuate tissue cutting RF powered electrode secured to and distally spaced from the distal end of the probe and a small dimensioned distal extremity which when an inner lumen thereof is subjected to a vacuum, secured tissue for the specimen to the surface of the distal extremity. A circular RF powered cutting electrode preferably secured to and spaced from the distal end of an outer sheath which when operatively energized with high frequency electrical power and longitudinally moved along the shaft of the probe member severs the tissue specimen secured to the surface of the distal extremity of the probe member from the tissue site. The outer sheath covers the separated specimen.

19 Claims, 10 Drawing Sheets

U.S. PATENT DOCUMENTS

| | | | |
|---|---|---|---|
| 4,276,885 A | 7/1981 | Tickner et al. | 424/9.52 |
| 4,294,241 A | 10/1981 | Miyata | |
| 4,294,254 A | 10/1981 | Chamness | |
| 4,311,143 A | 1/1982 | Komiya | |
| 4,331,654 A | 5/1982 | Morris | |
| 4,362,160 A | 12/1982 | Hiltebrandt | 128/303.15 |
| 4,503,855 A | 3/1985 | Maslanka | |
| 4,545,367 A | 10/1985 | Tucci | |
| 4,565,200 A | 1/1986 | Cosman | 128/642 |
| 4,576,162 A | 3/1986 | McCorkle | |
| 4,638,802 A | 1/1987 | Okada | |
| 4,647,480 A | 3/1987 | Ahmed | |
| 4,693,237 A | 9/1987 | Hoffman et al. | 128/899 |
| 4,718,419 A | 1/1988 | Okada | |
| 4,724,836 A | 2/1988 | Okada | |
| 4,813,062 A | 3/1989 | Gilpatrick | 378/162 |
| 4,847,049 A | 7/1989 | Yamamoto | |
| 4,863,470 A | 9/1989 | Carter | 623/8 |
| 4,909,250 A | 3/1990 | Smith | |
| 4,926,858 A | 5/1990 | Gifford, III et al. | |
| 5,007,908 A | 4/1991 | Rydell | |
| 5,024,617 A | 6/1991 | Karpiel | |
| 5,035,696 A | 7/1991 | Rydell | |
| 5,047,027 A | 9/1991 | Rydell | 606/48 |
| 5,064,424 A | 11/1991 | Bitrolf | 606/46 |
| 5,066,295 A | 11/1991 | Kozak et al. | |
| 5,078,716 A | 1/1992 | Doll | |
| 5,080,660 A | 1/1992 | Buelna | |
| RE33,925 E | 5/1992 | Bales et al. | |
| 5,111,828 A | 5/1992 | Kornberg et al. | |
| 5,133,359 A | 7/1992 | Kedem | 128/754 |
| RE34,056 E | 9/1992 | Lindgren et al. | 128/754 |
| 5,147,307 A | 9/1992 | Gluck | |
| 5,158,561 A | 10/1992 | Rydell et al. | |
| 5,163,938 A | 11/1992 | Kambara et al. | |
| 5,196,007 A | 3/1993 | Ellman et al. | |
| 5,201,732 A | 4/1993 | Parins et al. | |
| 5,201,741 A | 4/1993 | Dulebohn | |
| 5,207,686 A | 5/1993 | Dolgin | |
| 5,224,488 A | 7/1993 | Neuffer | 600/564 |
| 5,236,410 A | 8/1993 | Granov et al. | |
| 5,281,218 A | 1/1994 | Imran | 606/21 |
| 5,281,408 A | 1/1994 | Unger | |
| 5,282,781 A | 2/1994 | Liprie | |
| 5,312,400 A | 5/1994 | Bales et al. | |
| 5,318,564 A | 6/1994 | Eggers | |
| 5,323,768 A | 6/1994 | Saito et al. | |
| 5,324,288 A | 6/1994 | Billings et al. | 606/45 |
| 5,334,381 A | 8/1994 | Unger | |
| 5,335,671 A | 8/1994 | Clement | |
| 5,344,420 A | 9/1994 | Hilal et al. | |
| 5,368,030 A | 11/1994 | Zinreich et al. | 324/309 |
| 5,376,094 A | 12/1994 | Kline | |
| 5,380,321 A | 1/1995 | Yoon | |
| 5,395,312 A | 3/1995 | Desai | |
| 5,395,319 A | 3/1995 | Hirsh et al. | |
| 5,415,656 A | 5/1995 | Tihon et al. | 606/46 |
| 5,417,687 A | 5/1995 | Nardella et al. | 606/32 |
| 5,417,697 A | 5/1995 | Wilk et al. | |
| 5,422,730 A | 6/1995 | Barlow et al. | |
| 5,423,814 A | 6/1995 | Zhu et al. | |
| 5,431,649 A | 7/1995 | Mulier et al. | 606/41 |
| 5,433,204 A | 7/1995 | Olson | |
| 5,437,665 A | 8/1995 | Munro | |
| 5,441,503 A | 8/1995 | Considine et al. | |
| 5,462,553 A | 10/1995 | Dolgin | |
| 5,470,308 A | 11/1995 | Edwards et al. | 604/22 |
| 5,484,436 A | 1/1996 | Eggers et al. | |
| 5,487,385 A | 1/1996 | Avitall | 600/374 |
| 5,494,030 A | 2/1996 | Swartz et al. | 128/632 |
| 5,501,654 A | 3/1996 | Failla et al. | |
| 5,526,822 A | 6/1996 | Burbank et al. | |
| 5,527,331 A | 6/1996 | Kresch et al. | |
| 5,538,010 A | 7/1996 | Darr et al. | |
| 5,542,948 A | 8/1996 | Weavers et al. | |
| 5,549,560 A | 8/1996 | Van de Wijdeven | |
| 5,607,389 A | 3/1997 | Edwards et al. | |
| 5,611,803 A | 3/1997 | Heaven et al. | |
| 5,636,255 A | 6/1997 | Ellis | |
| 5,643,246 A | 7/1997 | Leeb et al. | |
| 5,643,282 A | 7/1997 | Kieturakis | |
| 5,646,146 A | 7/1997 | Faarup et al. | |
| 5,649,547 A | 7/1997 | Ritchart et al. | 128/754 |
| 5,665,085 A | 9/1997 | Nardella | |
| 5,674,184 A | 10/1997 | Hassler, Jr. | |
| 5,676,925 A | 10/1997 | Klaveness et al. | |
| 5,687,739 A | 11/1997 | McPherson et al. | 600/567 |
| 5,688,490 A | 11/1997 | Tournier et al. | |
| 5,715,825 A | 2/1998 | Crowley | 128/602.06 |
| 5,720,763 A | 2/1998 | Tovey | 606/198 |
| 5,741,225 A | 4/1998 | Lax et al. | 604/22 |
| 5,769,086 A | 6/1998 | Ritchart et al. | 128/753 |
| 5,772,660 A | 6/1998 | Young et al. | |
| 5,775,333 A | 7/1998 | Burbank et al. | |
| 5,782,764 A | 7/1998 | Werne | 600/411 |
| 5,782,775 A | 7/1998 | Milliman et al. | 600/567 |
| 5,794,626 A | 8/1998 | Kieturakis | 128/754 |
| 5,797,907 A * | 8/1998 | Clement | 606/45 |
| 5,800,378 A | 9/1998 | Edwards et al. | 602/22 |
| 5,810,806 A | 9/1998 | Ritchart et al. | |
| 5,853,366 A | 12/1998 | Dowlatshahi | 600/434 |
| 5,876,340 A | 3/1999 | Tu et al. | 600/439 |
| 5,902,272 A | 5/1999 | Eggers et al. | 604/114 |
| 5,925,044 A | 7/1999 | Hofmann et al. | |
| 5,928,164 A | 7/1999 | Burbank et al. | |
| 5,947,964 A * | 9/1999 | Eggers et al. | 606/41 |
| 5,964,716 A | 10/1999 | Gregoire et al. | 600/564 |
| 5,972,002 A | 10/1999 | Bark et al. | 606/140 |
| 5,984,919 A | 11/1999 | Hilal et al. | 606/45 |
| 6,004,269 A | 12/1999 | Crowley et al. | 600/439 |
| 6,050,955 A | 4/2000 | Bryan et al. | |
| 6,056,700 A | 5/2000 | Burney et al. | 606/167 |
| 6,063,082 A | 5/2000 | DeVore et al. | 606/45 |
| 6,120,462 A | 9/2000 | Hibner et al. | |
| 6,142,955 A | 11/2000 | Farascioni et al. | |
| 6,161,034 A | 12/2000 | Burbank et al. | 600/431 |
| 6,234,177 B1 | 5/2001 | Barsch | 128/897 |

FOREIGN PATENT DOCUMENTS

| | | |
|---|---|---|
| GB | 2311468 A | 2/1997 |
| GB | 2311468 A | 2/1997 |
| GB | 0 983 749 | 3/2000 |
| WO | 93/14712 | 5/1993 |
| WO | 93/13718 | 7/1993 |
| WO | PCT/GB94/01536 | 7/1994 |
| WO | PCT/GB94/01537 | 7/1994 |
| WO | 95/02371 | 1/1995 |
| WO | 96/08208 A1 | 3/1996 |
| WO | 98/06346 | 2/1998 |
| WO | 98/08441 | 3/1998 |
| WO | 99/30764 | 6/1999 |
| WO | 99/44506 | 9/1999 |
| WO | 00/16697 | 3/2000 |

OTHER PUBLICATIONS

Blackwell Science Ltd., "The Loop Electrode: New Device for US–Guided Interstitial Tissue Ablation Using Radio Frequency Electrosurgery–An Animal Study" 1996 *Min Incas Ther & Allied Technol* 5: 511–516.

F. Burbank, M.D., "Sterotactic Breast Biopsy: Its History, Its Present, and Its Future", *The American Surgeon*, Feb. 1996, vol. 62, pp. 128–150.

V. Fucci et al. "Large Bowel Transit Times Using Radiopaque Markers in Normal Cats", *J. of Am. Animal Hospital Assn.*, Nov.–Dec. 1995 31 (6) 473–7.

Timothy J. Micklos, "Percutaneous Biopsy Techniques", *Manual of Oncologic Therapeutics*, (1989/1990), pp. 39–42.

N. E. Schindlbeck et al., "Measurement of Colon Transit Time", *J. of Gstroenterology*, No. 28, pp. 399–404, 1990.

Whitman et al., "Coaxial Core Needle Biopsy Under Mammographic Guidance: Indications and Applications", AJR:171, Jul. 1998, pp. 67–70.

English Translation of German Application DE 195 28 440 A1, published Aug. 2, 1995.

International Search Report for PCT, US 99/21416 mailed May 19, 2000.

Written Opinion mailed Jul. 18, 2000, PCT Ruel 66, for International Application PCT/US/9921416.

International Search Report, PCT/US01/43360.

* cited by examiner

BIOPSY DEVICE AND METHOD OF USE

This application is a continuation-in-part of application Ser. No. 09/477,255, filed Jan. 4, 2000, and application Ser. No. 09/159,467, filed Sep. 23, 1998, now U.S. Pat. No. 6,261,241, which is a continuation-in-part of application Ser. No. 09/057,303, filed Apr. 8, 1998, now U.S. Pat. No. 6,331,166, which claims the benefit of provisional patent application Ser. No. 60/076,973, filed Mar. 3, 1998, all of which applications are hereby incorporated herein by reference in their entirety and from which priority is hereby claimed under 35 U.S.C. §§119(e) and 120.

BACKGROUND OF THE INVENTION

The present invention relates generally to the field of biopsy devices and the methods of using such devices. More specifically, it relates to a device and method for accessing a targeted site of pathologically suspect tissue mass within a patient's body, so as to facilitate the taking of a specimen of the tissue mass.

In diagnosing and treating certain medical conditions, such as potentially cancerous tumors, it is usually desirable to perform a biopsy, in which a specimen of the suspicious tissue is removed for pathological examination and analysis. In many instances, the suspicious tissue is located in a subcutaneous site, such as inside a human breast. To minimize surgical intrusion into the patient's body, it is desirable to be able to insert a small instrument into the patient's body to access the targeted site and then extract the biopsy specimen therefrom.

After removing the tissue specimens, additional procedures may be performed at the biopsy site. For example, it may be necessary to cauterize or otherwise treat the cavity which results from tissue specimen removal to stop bleeding and reduce the risk of infection or other complications. Also, it may be advantageous to mark the site for future surgical procedures should pathological tests performed on the biopsy specimen indicate surgical removal or other treatment of the suspected tissue mass from which the specimen was removed. Such marking can be performed, for example, by the apparatus and method disclosed and claimed in co-pending U.S. patent application Ser. No. 09/343,975, filed Jun. 30, 1999, entitled "Biopsy Site Marker and Process and Apparatus for Applying It," which is hereby incorporated by reference in its entirety.

Electrosurgical techniques have been used in a variety of circumstances, including certain types of biopsy procedures. In electrosurgery, high frequency electrical energy is applied through an active electrode to patient tissue. The electrical energy flows through the tissue from the active electrode to a return electrode which is in contact with the patent's tissue and which may be on the exterior of the patient's body or intracorporeally disposed. Typically, the return electrode is attached to the patient at a point remote from where the primary or active electrode contacts the tissue. The tissue adjacent the primary electrode is ablated, to form an opening in the tissue. An electrosurgical biopsy instrument is disclosed and claimed in U.S. patent application Ser. No. 09/159,467 for "Electrosurgical Biopsy Device and Method," assigned to the assignee of the subject application, and which is hereby incorporated by reference in its entirety.

SUMMARY OF THE INVENTION

This invention is directed to a biopsy device that provides ready access to a targeted tissue site within a patient's body and provides for the separation and capture of a tissue specimen from the target tissue site. More specifically, the biopsy device provides for a split tissue specimen which greatly facilitates a accurate pathological examination upon its removal from the patient's body.

The biopsy device of the invention generally includes an elongated probe having a proximal end and a distal end and an inner lumen extending therein. A distal probe section is provided which has transverse dimensions less than adjacent portions of the probe and which has one and preferably a plurality of apertures in a wall thereof in fluid communication with the probe's inner lumen. A circular electrode or a pair of opposed semicircular electrodes are slidably disposed about the probe member and are configured for longitudinal translation along a length and preferably the entire length of the small dimensioned distal probe section. The electrode or electrodes are disposed in a plane or planes which are perpendicular and transverse to the longitudinal axis of the probe.

The proximal end of the probe is configured to allow the inner lumen of the probe to be connected to a vacuum source, so that when a vacuum is applied to the inner lumen, tissue adjacent to the small dimensioned distal probe section is pulled into contact with the distal probe section through action of the vacuum through the apertures thereof and thereby fix the tissue specimen to the distal probe section. With the tissue of the specimen secured to the distal probe section, the circular or semicircular electrodes powered by high frequency (RF) electrical power may then be advanced distally to thereby separate the tissue specimen from the tissue bed to which the tissue is secured and supported. The probe and the tissue specimen secured thereto may then be withdrawn from the patient.

In present embodiment of the invention, the biopsy device has a thin, arcuate shaped distal electrode connected to the distal end of the probe and spaced distally therefrom as disclosed in copending applications Ser. No. 09/477,255, filed on Jan. 4, 2000 and Ser. No. 09/057,303 filed on Apr. 8, 1998, which are hereby incorporated herein in their entirety. The distal arcuate electrode lies in a plane that is parallel to and generally passes through a longitudinal axis of the elongated probe. The cordal dimension of the distal electrode is at least the same dimension as the diameter of the distal end of the elongated probe, preferably greater than the diameter of the distal end to ensure that an opening is made through the tissue to the target site and through the suspicious tissue by the electrode which is large enough to allow the biopsy device to be readily advanced. Moreover, because the distal electrode passes through the desired tissue for the specimen, it makes a planar cut through the desired specimen, so that when the circular or semicircular electrodes are advanced over the small dimensioned distal probe section to cut the specimen from the supporting tissue, the specimen is split or is separated into two half specimens.

In a presently preferred embodiment the biopsy device is provided with an outer sheath that is slidably disposed along a length of the probe so as to cover the small dimensioned distal probe section during advancement through tissue and to open and allow specimen tissue to be pulled into contact with the small dimensioned distal probe section when a vacuum is applied to the inner lumen of the probe and the tissue of the specimen is severed from the adjacent supporting tissue by the longitudinal translation of the RF powered circular or semicircular electrodes. The electrodes may be secured to the distal end of the sheath so that the specimen(s) can be separated from the adjacent tissue while the sheath closes over the small dimensioned distal probe section thereby capturing the severed specimen(s) within the interior of the sheath. The biopsy device may then withdrawn from the patient, and once withdrawn, the specimen or specimen halves secured to the distal probe section maybe removed for subsequent pathological examination.

The distal electrode is connected by means of an electrical conductor which extends to the proximal extremity of the probe, preferably through the inner lumen of the probe to a high frequency, e.g. RF, electrical power. The proximal circular electrode or semicircular electrodes may have their own supporting structure or may be supported as described above from the distal end of the outer sheath. An elongated electrical conductor connects the proximal circular electrode or a pair of elongated electrical conductors connects the proximal electrode to a high frequency, e.g. RF, electrical power which may be the same power source which powers the distal electrode or a separate power source. When the proximal circular electrode or semicircular electrodes are secured to the distal end of the outer sheath, the conductor(s) which connects the proximal electrode(s) may extend through the wall of the outer sheath. The high frequency power for the proximal electrode or electrodes is usually greater than the high frequency power required by the distal electrode. However, generally the proximal electrode(s) are operated at a different time in the procedure so a single power source can be readily programmed to operate at the different electrical power levels required by the electrodes of the present device.

The probe, the proximal electrode and the outer sheath are preferably configured as a disposable unit which may be hand operated or powered by a hand unit connected to a suitable controller.

These and other advantages of the invention will become more apparent from the following detailed description of the invention and the accompanying exemplary drawings.

DETAILED DESCRIPTION OF THE INVENTION

Reference is made to FIGS. 1–14 which illustrate a biopsy device 10 embodying features of the invention. The device 10 generally includes an elongated probe member 11, a first tissue cutting electrode 12, a second tissue cutting electrode 13 and an outer sheath 14 slidably disposed about the probe 11. In one embodiment of the invention shown in FIG. 1, the device 10 is a disposable device and is configured to be mounted on a handle 15 which provides electrical power and control to the device.

The probe member 11 has a proximal section 16 configured for slidable disposition within the inner lumen 17 of the outer sheath 14 and a distal section 18 which includes a distal extremity 20 which is configured to secure tissue from a tissue site which is to form the specimen and an enlarged distal end 21 to which the second electrode 13 is secured.

Figure 6:
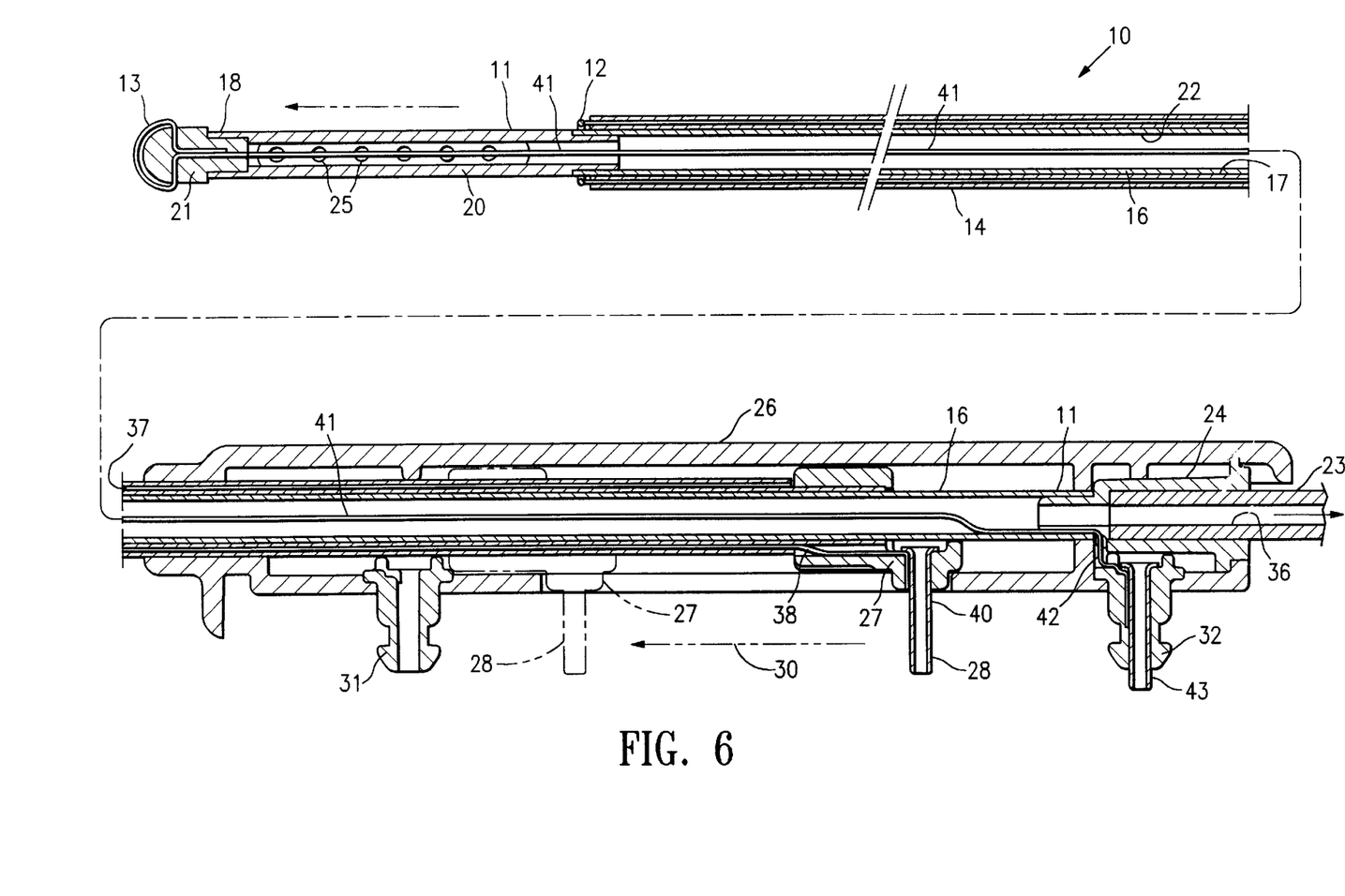
FIG. 6 is a longitudinal cross-sectional view of the device shown in FIG. 2 taken along the lines 6—6.

As shown in more detail in FIGS. 6–10, the probe member 11 is provided with an inner lumen 22 which extends from the distal extremity 20 to a connection member 23 on the proximal end 24 of the probe member 11 and which is in fluid communication with the plurality of aspiration ports 25 provided on the distal extremity 20 of the probe member 11. The proximal end 24 of the probe member 11 and the connection member 23 are secured within the housing 26 as best shown in FIG. 6.

The outer sheath 14 is slidably disposed about the proximal section of the probe member 11 and has a proximal end secured to a slidable collar 27 within the housing 26. The collar 27 is provided with an arm 28 which is configured to seat within a receiving opening on a driver (not shown) provided in the handle 15. The collar 27 is configured to be slidably disposed within the housing so that the driver on the handle can move the arm 28 and as a result translate the outer tubular sheath as shown by the arrow 30 in FIG. 6 between an opened and closed (shown in phantom) configuration.

Figure 1:
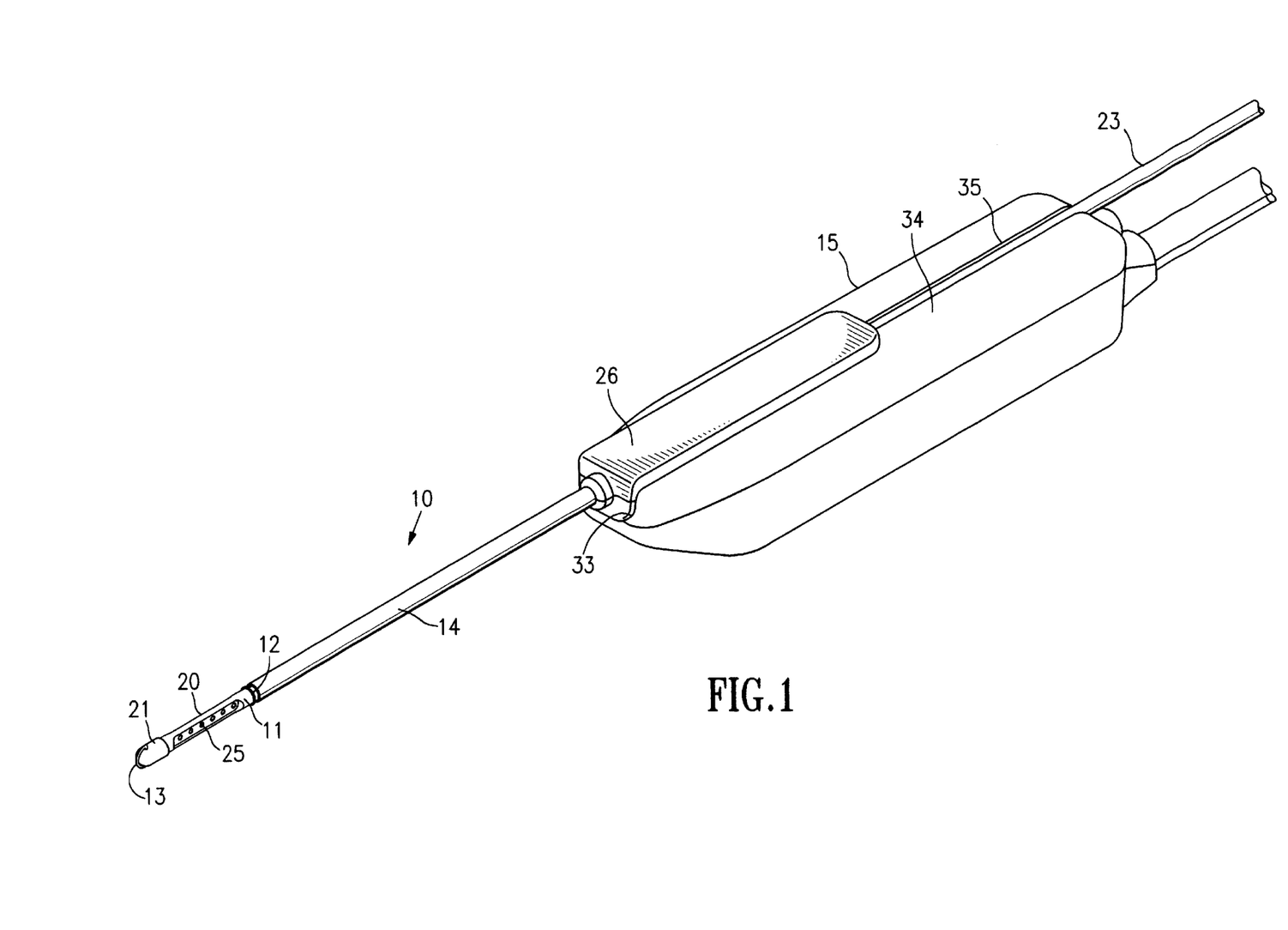
FIG. 1 is a perspective view of a removable biopsy device having features of the invention seated within a handle with the outer sheath of the device in an opened configuration.
Figure 2:
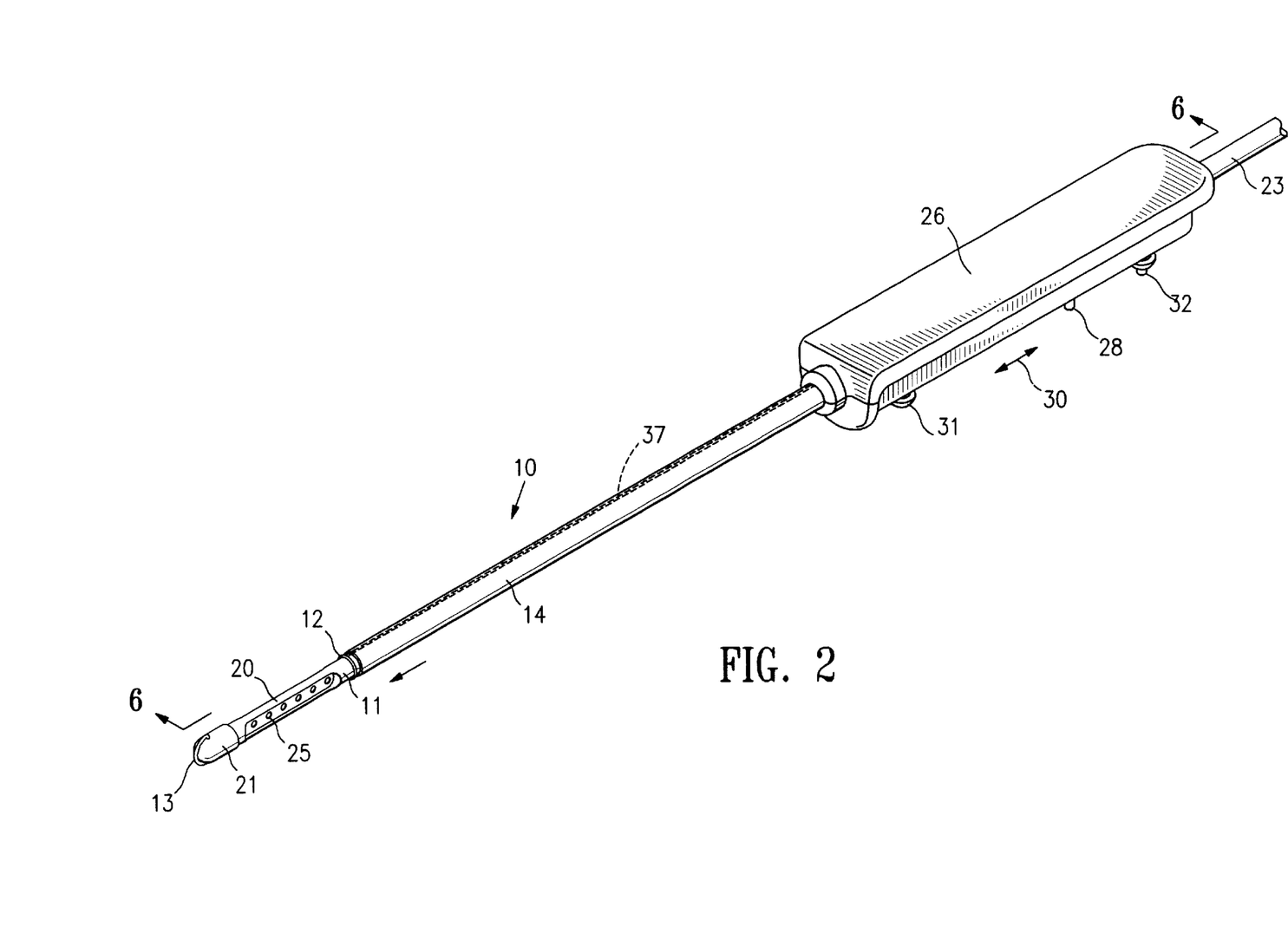
FIG. 2 is a perspective view of the biopsy device shown in FIG. 1 removed from the handle.
Figure 3:
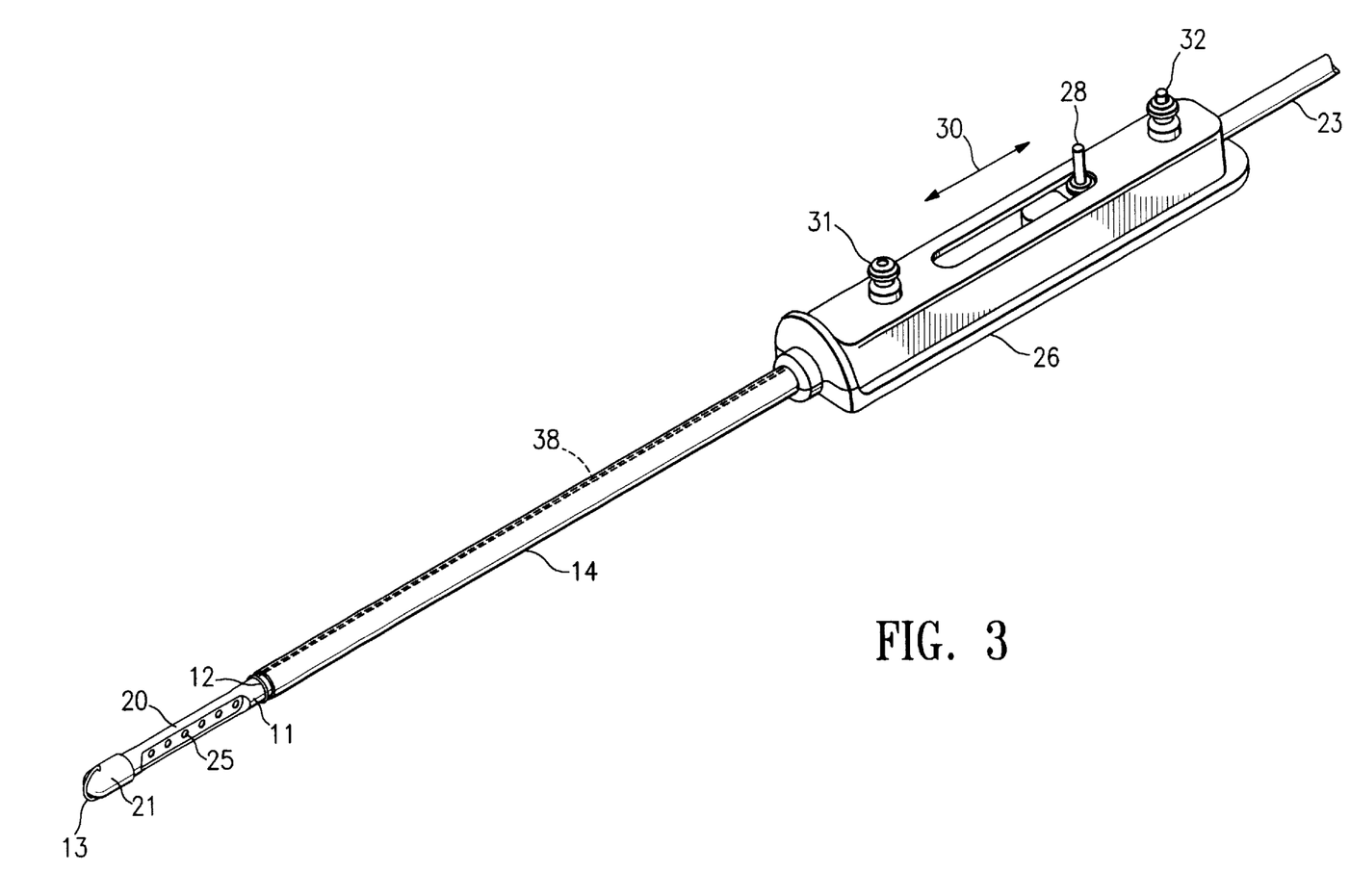
FIG. 3 is a perspective view of the biopsy device shown in FIG. 2 rotated 180° about its longitudinal axis.
Figures 4, 5:
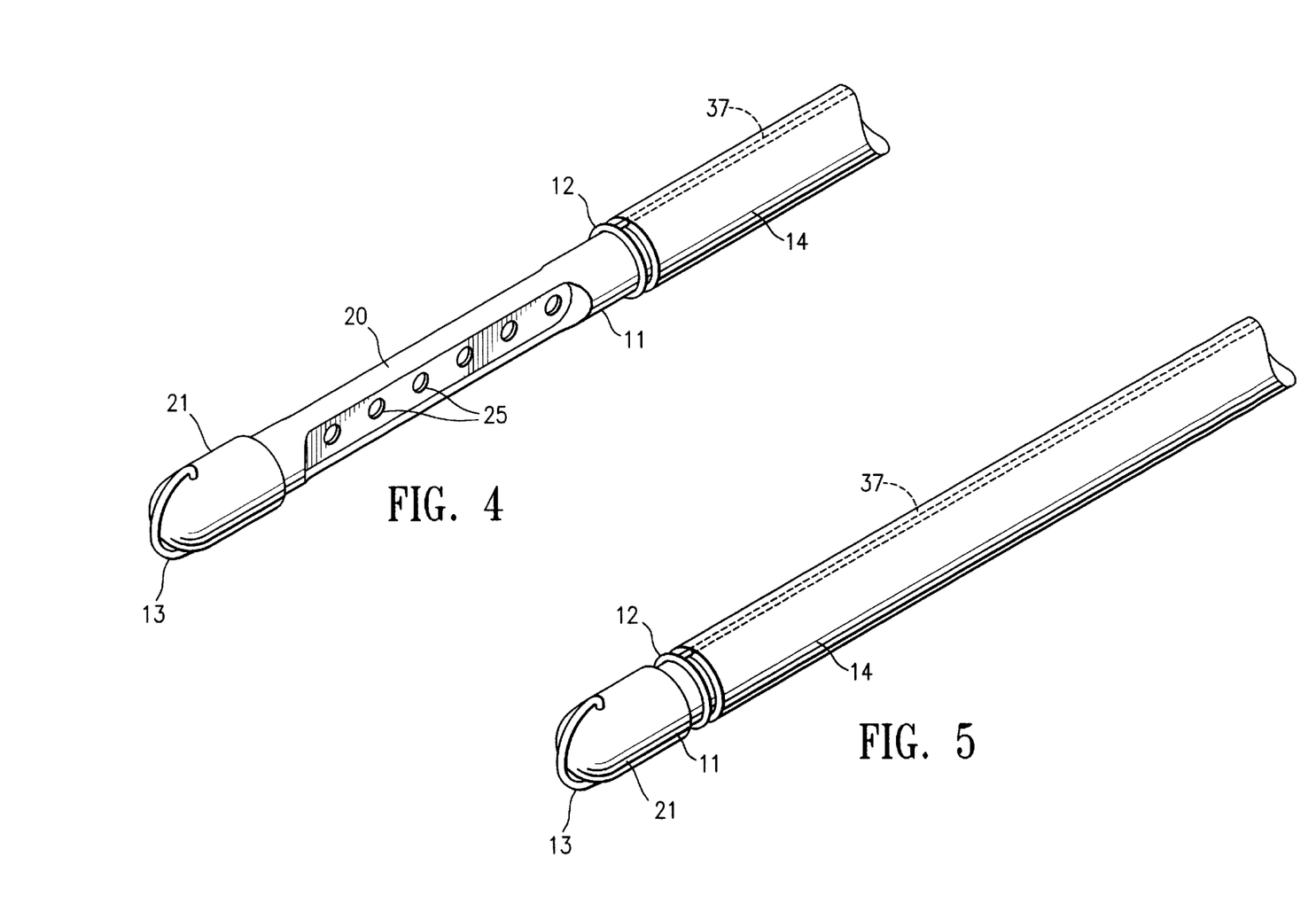
FIG. 4 is an enlarged perspective view of the distal section of the biopsy device shown in FIG. 2 with the outer sheath in an opened configuration.
FIG. 5 is an enlarged perspective view of the distal section of the biopsy device shown in FIG. 2 with the outer sheath in a closed configuration.

The housing 26 is provided with distal projection 31 and proximal projection 32 which are designed to tightly seat within receiving openings (not shown) provided in the handle to effect a snap fit of the housing 26 within a recess 33 provided in the upper surface 34 of handle as shown in FIG. 1. A second long recess 35 is provided in the upper surface 34 of handle 15 which is contiguous with recess 33 and which is configured to receive the connection member 23 tightly enough to prevent accidental excursions out of the recess. As shown in FIG. 6, the connection member 23 has an inner lumen 36 in fluid communication with the inner lumen 22 of the probe member 11.

The first electrode 12, which is circular and disposed about the probe member 11, is connected to electrical conductors and support elements 37 and 38 which extend through the wall of outer sheath 14. This construction allows the first electrode to travel longitudinally with the outer sheath over the distal extremity 20 of the probe member 11 and in this manner cut the tissue specimen held against the distal extremity by the action of a vacuum within the inner lumen 22 from the tissue site and at the same time cover the separated tissue specimen with the outer sheath so that the specimen can be removed with device 10 from the patient with the same movement.

As shown in FIG. 6, the proximal end(s) of the electrical conductors 37 and 38 are secured to the conducting tubular element 40 provided in the arm 28 of collar 27 which drives and withdraws the outer sheath 14.

Figure 7:
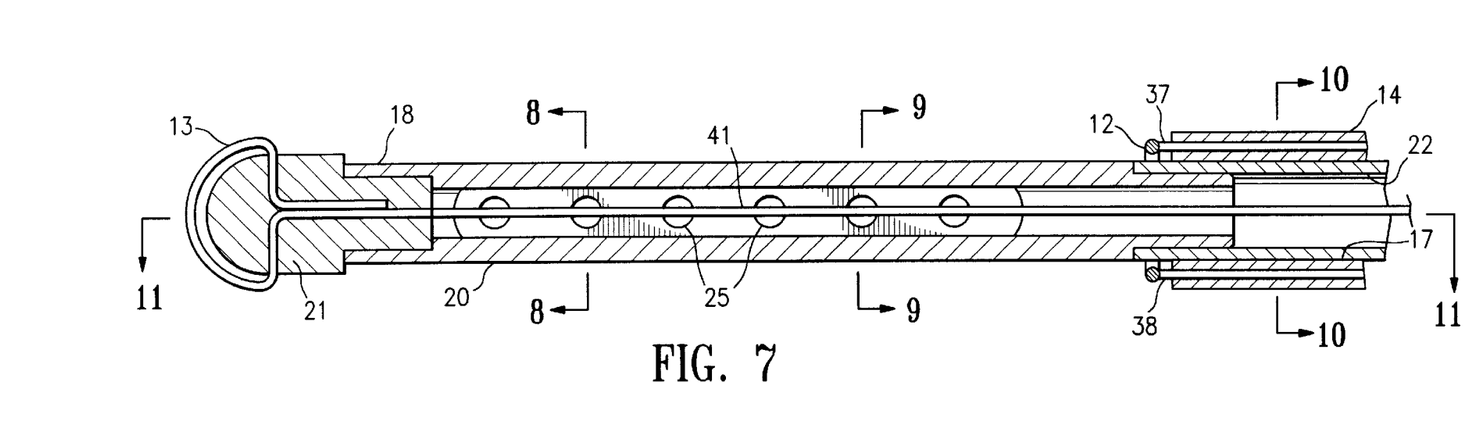
FIG. 7 is an enlarged longitudinal cross-sectional view of the distal section of the device shown in FIG. 6.
Figure 8:
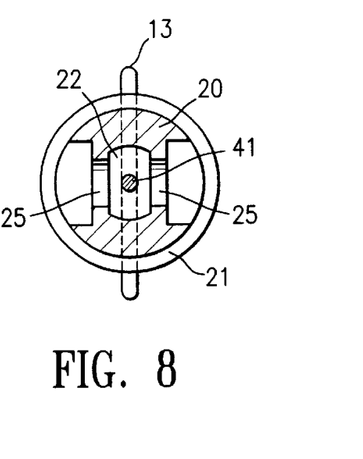
FIG. 8 is a transverse cross sectional view of the device shown in FIG. 7 taken along the lines 8—8.
Figure 9:
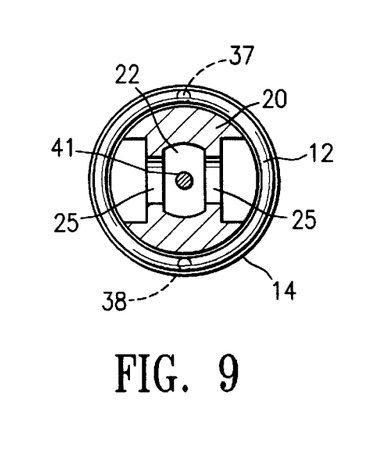
FIG. 9 is a transverse cross sectional view of the device shown in FIG. 7 taken along the lines 9—9.
Figure 10:
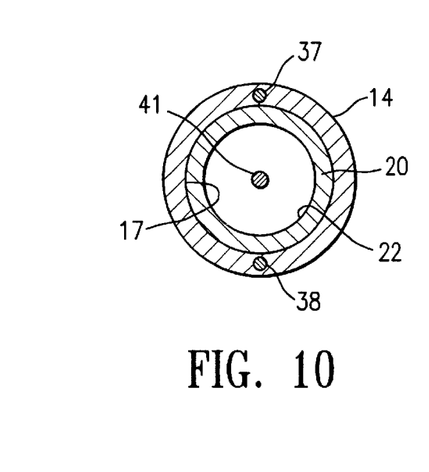
FIG. 10 is a transverse cross sectional view of the device shown in FIG. 7 taken along the lines 10—10.
Figure 11:
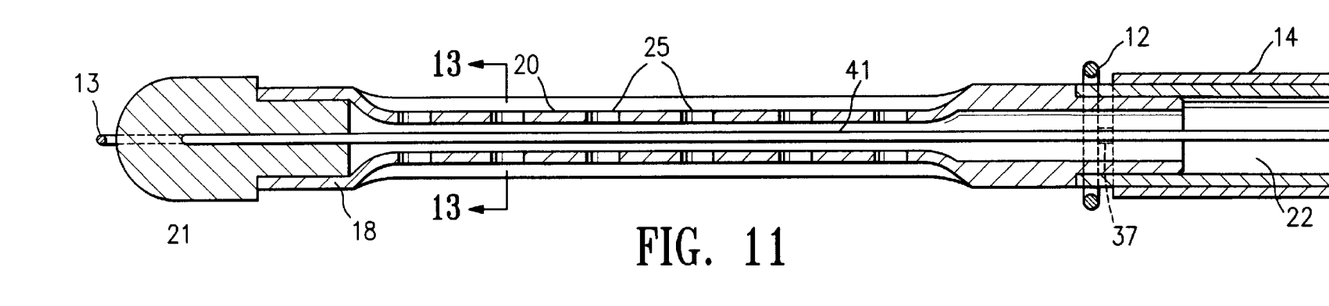
FIG. 11 is an enlarged longitudinal cross-sectional view of the distal section of the device shown in FIG. 6 rotated 90° from the view shown in FIG. 7.
Figure 12:
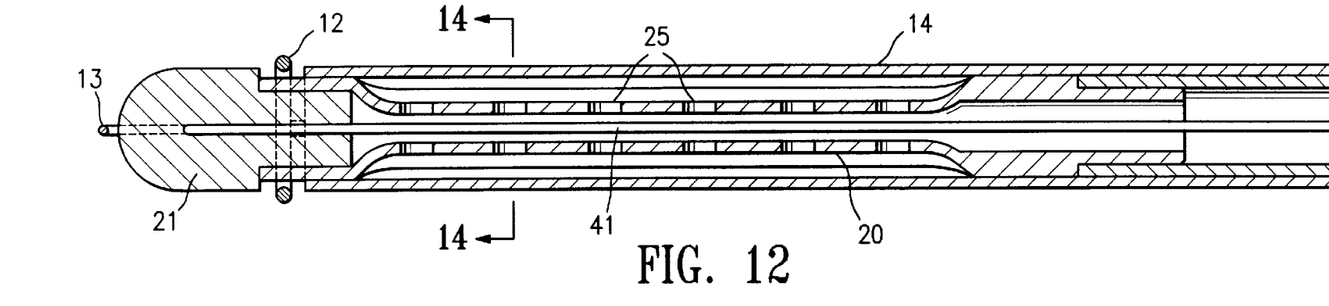
FIG. 12 is an enlarged longitudinal cross-sectional view of the distal section of the device as shown in FIG. 11 with the outer sheath in a closed configuration.
Figure 13:
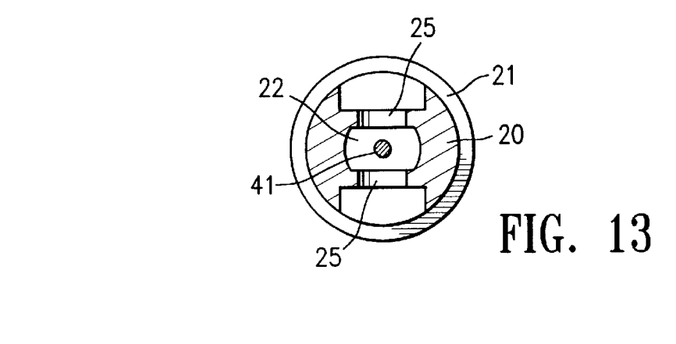
FIG. 13 is a transverse cross sectional view of the device shown in FIG. 1 1 taken along the lines 13—13.
Figure 14:
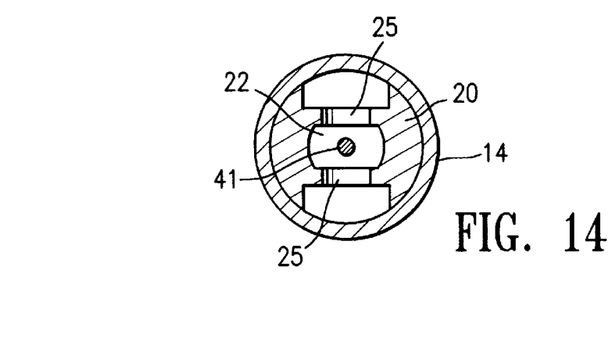
FIG. 14 is a transverse cross sectional view of the device shown in FIG. 12 taken along the lines 14—14.

The second electrode 13 has an arcuate portion which is spaced distally away from the distal end 21 and has a maximum chord (i.e. distance between the ends of the arcuate portion) which is preferably larger than the maximum diameter of the distal end. The maximum width of the second electrode 13 is preferably about 20 to about 50% greater than the maximum outside transverse dimension of the distal end 21 of the probe 11. The second electrode 13 can be spaced distally from an outer surface of the distal end 21 by a distance of about 0.01 to about 0.05 inch, preferably about 0.02 to about 0.04 inch. As best shown in FIGS. 6 and 7, the arcuate second electrode 13 is formed out of the distal extremity of electrical conductor 41. The proximal end 42 of the conductor 41 is electrically connected to tubular conductor 43 provided in the proximal projection 32 of housing 26 as shown in FIG. 6.

The shaft of the device 10 which extends out from the housing 26 may have a length of about 3 to about 15 cm, preferably, about 5 to about 13 cm, and more specifically, about 8 to about 9 cm for breast biopsy use. To assist in properly locating the shaft of device 10 during advancement thereof into a patient's body, (as described below), the distal extremity 20 of the probe and the outer sheath 14 may be provided with markers at desirable locations that provide enhanced visualization by ultrasound or X-ray. For ultrasonic location an echogenic polymer coating that increases contrast resolution in ultrasound imaging devices such as ECHOCOAT™ by STS Biopolymers, of Henrietta, N.Y. In addition, the surfaces of the device in contact with tissue may be provided with a suitable lubricious coating such as a hydrophilic material or a flouropolymer.

The proximal portion of the probe 11 generally has an outer dimension of about 3 to about 10 mm and a inside dimension of about 2 to about 6 mm and it may be desirable in some embodiments to have a close fit between the proximal section of the probe 11 and the inner lumen 17 of outer sheath 14 to avoid a gap there between which can catch or snag on adjacent tissue during advancement through tissue and impede advancement.

The first and second electrodes 12 and 13 can be generally conductive wire formed of metallic materials such as stainless steel. The shaft components from which the probe 11 and outer sheath 14 are formed may be conventional medical grade polymer materials such as polycarbonate and liquid crystal polymer (LCP), respectively.

Figure 15:
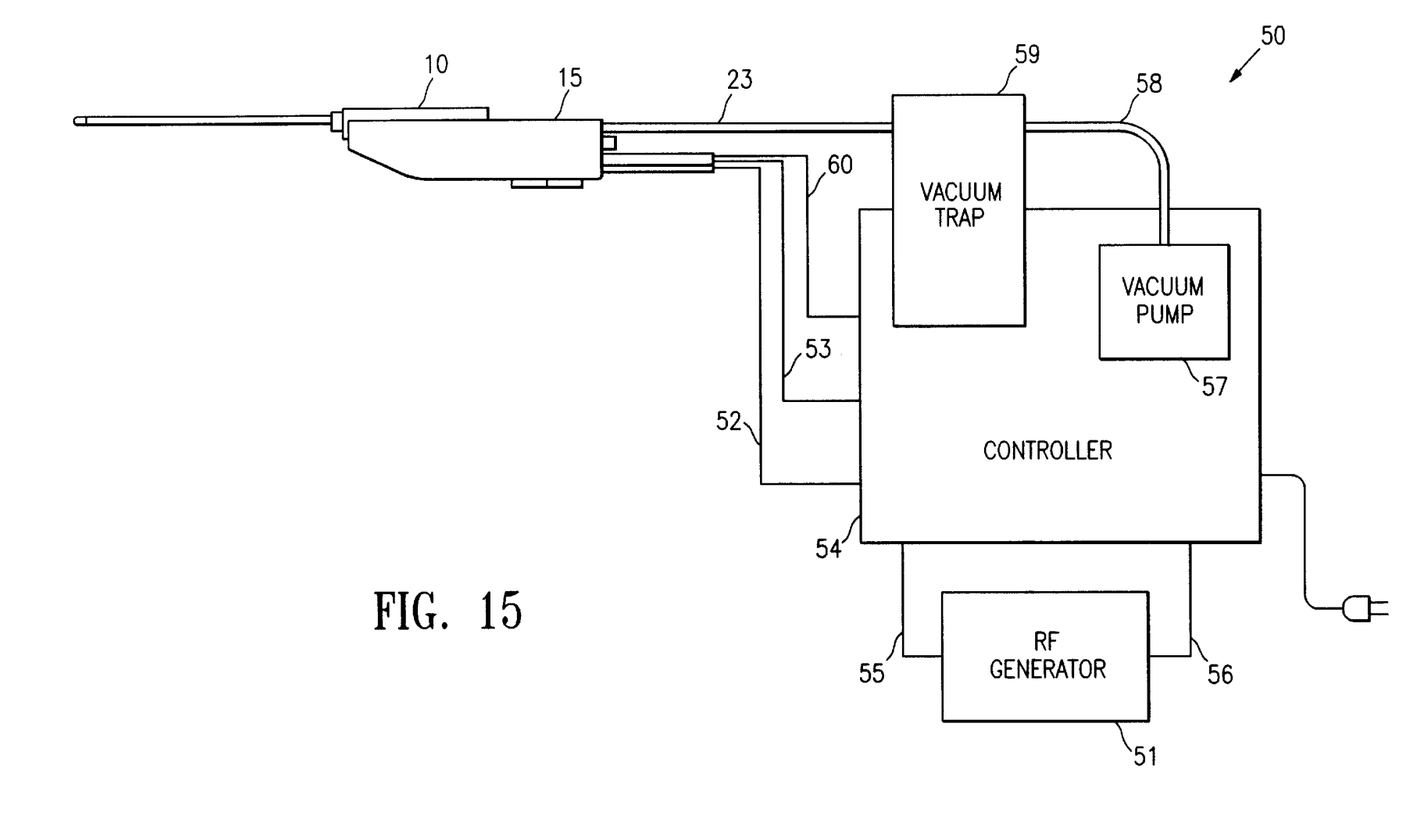
FIG. 15 schematically illustrates an operative system embodying the devices of the invention.

The biopsy device 10 may be use to obtain a tissue specimen utilizing the operation system 50 schematically shown in FIG. 15. The operating system 50 generally includes a high frequency (e.g. RF) electrical power generator 51, which is electrically connected to both the first and second tissue cutting electrodes 12 and 13 on the biopsy device 10 through conductors 52 and 53. The power output and the receiving element is controlled by the controller 54. The RF generator 51 is electrically connected to the controller through conductors 55 and 56 and preferably operates at about 300 to about 1000 KHz, specifically, about 700 to about 900 KHz and has a power output of about 50 to about 150 watts, preferably, about 80 to about 100 watts. Vacuum is generated by the vacuum pump 57 which is connected in a fluid flow relationship with the inner lumen (not shown) provided in conduit 58 which leads to a vacuum trap 59. Vacuum is applied to the inner lumen 22 of the probe member 11 through inner lumen 36 of connection member 23 connected to the vacuum trap. A meter actuation and control cable 60 is provided to power and control the actuation elements in handle 15.

Figure 16:
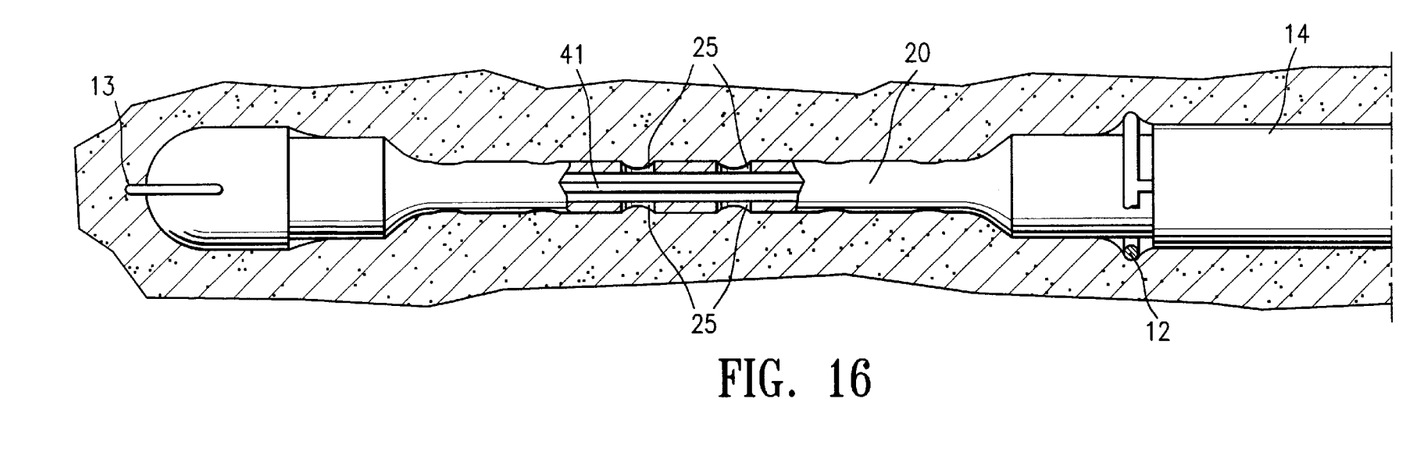
FIG. 16 is a transverse cross sectional view of the device shown in FIG. 12 disposed with a tissue site and tissue at the site held against the surface of the distal extremity by the action of a vacuum within the inner lumen of the probe.
Figure 17:
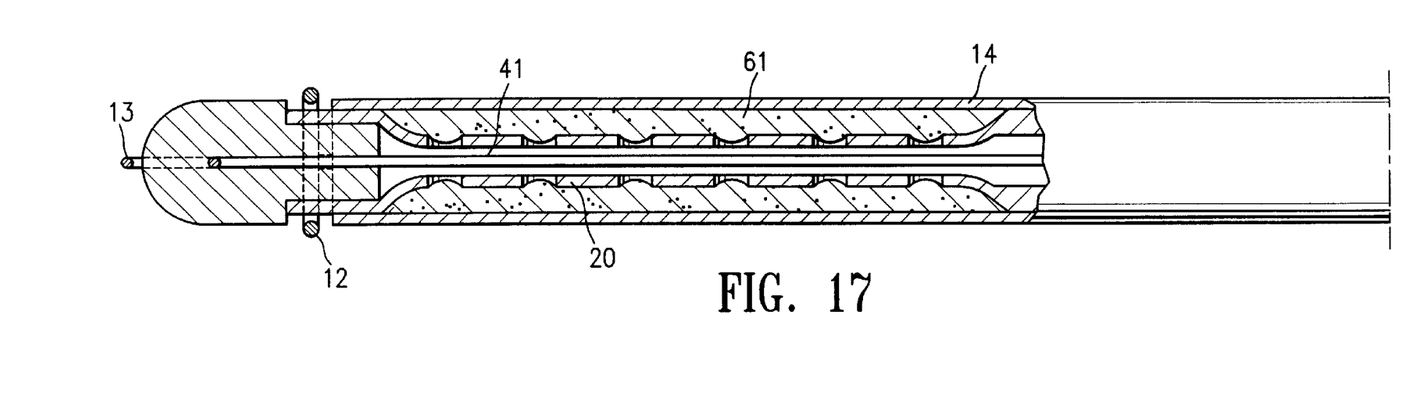
FIG. 17 is a transverse cross sectional view of the device shown in FIG. 15 with the first electrode and outer sheath in a closed configuration with a separated tissue specimen within the space. between the distal extremity 20 and the interior of the outer sheath 14.

A tissue specimen is obtained with the device 10 by pressing the second electrode 13 of the device 10 against an exterior site on the patient's skin proximate to the tissue site where the specimen is to be obtained. High frequency electrical power from the generator 51 passes through the electrical conductor 41 to energize the second electrode 13 and the device 10 with the second electrode energized is advanced through the tissue until the distal end 21 of the device has passed through the tissue which is to form the specimen. The action of the energized second electrode 13 forms a planar cut through the desired tissue bed and allows the probe to readily pass through the tissue. Very little collateral tissue damage is done by the accessing second electrode 13 at the margins where the tissue cut is made. It should be noted that many physicians may prefer to first make an incision with a scalpel through the patient's skin and expose subcutaneous tissue before passing the device 10 through the tissue on the belief that the cutting action of a high frequency powered electrode such as second electrode 13 can cause excessive scar tissue formation on the access site. The device is preferably advanced through the patient's tissue to the specimen site with the outer sheath 14 in a closed configuration. Once the device 10 is in the desired location, the outer sheath 14 can be withdrawn to an opened configuration to expose the distal extremity 20 of the probe 11 by action of the driver (not shown) operatively connected to the arm 28 of collar 27. With the distal extremity 20 of the probe 11 exposed, a vacuum can be generated within the inner lumen 22 of probe 11 by the action of vacuum pump 57. The vacuum generated in the inner lumen 22, acting through the ports 25 in the distal extremity 20 draws tissue at the site against the surface of the distal extremity and holds the tissue against the surface as shown in FIG. 16. The first electrode 12 may then be energized by high frequency electrical power and then driven distally along with the outer sheath 14 to which the electrode 12 is secured to sever a generally cylindrical shaped tissue specimen 61 from the adjacent tissue site and cover the severed tissue specimen with the sheath 14 as shown in FIG. 17. The biopsy device may then be removed from the patient. Due to the planar cut made by the second electrode 13 through the tissue from which the specimen is to be obtained, the cylindrical specimen 61 is a split specimen which greatly aids in its evaluation. It may be desirable to provide an accessing cannula on the exterior of the outer sheath 14 which can be left in the patient with its distal end at the site from which the specimen was obtained to allow a marker or other device to be deposited at the site in case further procedures or treatments are necessary or desirable and the site has to be located at a later time. After the biopsy procedure is completed, the incision formed by the initial cut through the patient's skin appropriately closed.

Figures 18, 19:
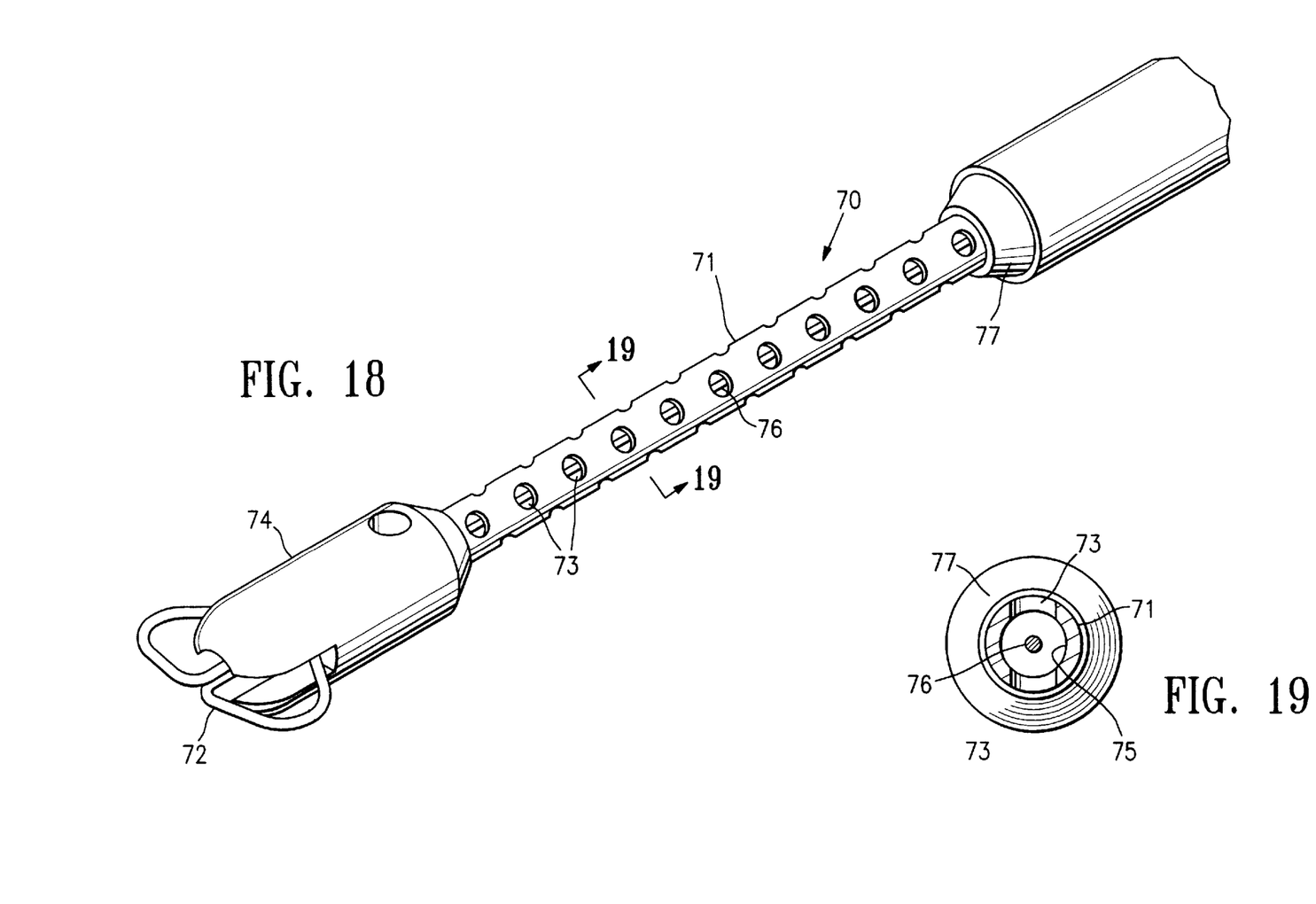
FIG. 18 is a perspective view of an alternative probe member for the biopsy device.
FIG. 19 is a transverse cross-sectional view of the biopsy device shown in FIG. 18 taken along the lines 19—19.

An alternative probe member 70 embodying features of the invention is depicted in FIGS. 18 and 19. In this alternative the distal extremity 71 of the probe device 70 is of tubular construction as shown. The tissue cutting electrode 72 on the distal end of the probe member 70 has an expandable construction which is disclosed in copending application Ser. No. 09/477,255, filed Jan. 4, 2000, entitle Apparatus and Method for Accessing A Biopsy Site, by Burbank et al., which is incorporated herein by reference in its entirety. The tubular distal extremity 71 has a plurality of ports 73 which are in fluid communication with an inner lumen 75. Cutting electrode 72 is secured to the enlarged distal end 74. An electrical conductor 76 (shown in FIG. 19) extends through inner lumen 75 and is electrically connected to electrode 72. An outer sheath 77 extends about the probe member 70. The probe 70 is used in the same manner described above with an outer sheath and circular tissue cutting electrode for the embodiment shown in FIGS. 1–14. The outer sheath may be configured to allow the probe 70 to be withdrawn with the specimen for specimen removal leaving the distal end of the sheath located at the biopsy site, thus eliminating the need for an accessing cannula.

Those skilled in the art will recognize that various modifications may be made to the specific embodiments illustrated above. In addition, it will be readily appreciated that other types of instruments may be inserted into the tissue site through the outer sheath or a suitable cannula in addition to or in place of the instruments described above. These and other modifications that may suggest themselves are considered to be within the scope of the claims that follow.

What is claimed is:

1. An elongated device for separation of a tissue specimen from a target tissue site, comprising:
   a. an elongated probe which has a proximal end, a distal end, a longitudinal axis, an inner lumen extending within the probe and which has a distal extremity with at least one aperture in a wall thereof that is in fluid communication with the inner lumen extending within the probe and with a transverse dimension substantially less than portions of the probe distal to the distal extremity; and
   b. a first tissue cutting electrode which is at least partially disposed about the elongated probe, which lies in a plane transverse to the longitudinal axis of the probe, which has an inner dimension substantially greater that the small transverse dimension of the distal extremity of the probe, which is configured for longitudinal movement along a length of the distal extremity of the probe and which is configured to be electrically connected to a high frequency power source.

2. The elongated device of claim 1 including a fluid connection on the proximal end of the elongated probe which is in fluid communication with the inner lumen extending within the probe and which is configured for fluid communication with a vacuum source.

3. The elongated device of claim 1 wherein the first electrode is electrically connected to the power source by a first elongated electrical conductor having a distal end electrically connected to the first electrode and a proximal end configured for electrical connection to a source of high frequency electrical power source.

4. The elongated device of claim 1 including a second tissue cutting electrode spaced distal to the distal end of the elongated inner probe to facilitate advancement of the probe through tissue to the target site.

5. The elongated device of claim 4 including a second elongated electrical conductor having a distal end electrically connected to the second electrode and a proximal end configured for electrical connection to a high frequency electrical power source.

6. The elongated device of claim 4 wherein the second electrode has an arcuate shape and has a chord length at least as great as the transverse dimension of the probe distal to the distal extremity.

7. The elongated device of claim 4 wherein the second electrode lies in a plane which is parallel to the longitudinal axis of the probe.

8. The elongated device of claim 2 wherein the distal extremity has a plurality of apertures which are in fluid communication with the inner lumen.

9. The elongated device of claim 8 wherein the distal extremity of the probe has a circular transverse cross sectional shape.

10. The elongated device of claim 1 including an outer sheath which as proximal and distal ends, which has an inner lumen extending therein, which is slidably disposed about the elongated probe member and which is configured to be advanced over the distal extremity and thereby capture any tissue separated by the first electrode.

11. The elongated device of claim 10 wherein the first electrode is secured to the distal end of the outer sheath.

12. The elongated device of claim 11 including a first electrical conductor having a distal end electrically connected to the first electrode and a proximal end configured to be electrically connected to an electrical power source.

13. The elongated device of claim 12 wherein the first electrical conductor extends longitudinally through a wall of the outer sheath.

14. An elongated tissue biopsy device, comprising:
   a. an elongated probe which has a proximal end and a distal end, which has a longitudinal axis, which has an inner lumen extending within a portion of the probe and which has a distal extremity with at least one transverse dimension less than an adjacent portion of the probe distal to the distal extremity and with at least one aperture that is in fluid communication with the inner lumen extending within the probe;
   b. a proximal electrode which is at least partially disposed about the elongated probe, which lies in a plane that is transverse to the longitudinal axis and which is configured for longitudinal movement along a length of the small dimensioned distal probe section;
   c. a first elongated electrical conductor having a distal end electrically connected to the first electrode and a proximal end configured for electrical connection to a high frequency electrical power source;
   d. an arcuate second tissue cutting electrode which is spaced distal to the distal end of the probe, which has a chordal length at least as great as the largest transverse dimension of the distal end of the probe and which lies in a plane parallel to the longitudinal axis of the probe; and
   e. a second elongated electrical conductor having a distal end electrically connected to the second electrode and a proximal end configured for electrical connection to a high frequency electrical power source.

15. An elongated biopsy device, comprising:
   a. an elongated outer tubular member which has proximal and distal ends, a first port in the distal end, a second port in the proximal end and an inner lumen extending therein from the first port in the distal end to the second port in the proximal end;

b. a circular first electrode secured to the distal end of the outer tubular member;

c. an elongated first electrical conductor which has a distal end electrically connected to the circular first electrode and a proximal end configured for electrical connection to a high frequency electrical power source;

d. an elongated probe which is slidably disposed within the inner lumen of the outer tubular member, which has an inner lumen extending therein, having a distal extremity with at least one aperture that is in fluid communication with the inner lumen extending within the interior of the probe;

e. an arcuate second electrode which is spaced distally of the distal end of the elongated inner probe; and f. an elongated second electrical conductor which has a distal end electrically connected to the arcuate electrode and a proximal end configured for electrical connection to a high frequency electrical power source.

16. The biopsy device of claim 15 wherein the first elongated conductor extends through a wall of the outer tubular member.

17. The biopsy device of claim 16 wherein the second electrode has an expanded deployed configuration with a width greater than an outside transverse dimension of the distal end of the probe and a contracted configuration with a width that is equal to or less than an inside transverse dimension of the inner lumen of the outer tubular member.

18. A method of separating a specimen of tissue at a desired site within a patient's body, comprising:

a. providing an elongated biopsy device of claim 15;

b. energizing the second electrode while advancing the elongated biopsy device into the patient's body until the distal end of the device has been advanced at least partially into tissue at a desired site within the patient's body;

c. withdrawing the outer tubular member to expose the distal extremity of the probe;

d. applying a vacuum to the inner lumen of the probe to secure tissue to the distal extremity;

e. energizing the first electrode While distally advancing the first electrode over the distal extremity of the probe to separate a tissue specimen from the tissue site;

f. advancing the outer tubular member over the separated tissue specimen; and g. withdrawing the elongated device with the tissue specimen from the patient.

19. A method of obtaining a plurality of tissue specimens at a desired site within a patient's body, comprising:

a. providing an elongated biopsy device of claim 15 wherein the outer tubular member is configured to allow the probe member to be withdrawn therethrough;

b. energizing the second electrode while advancing the elongated biopsy device in the patient's body until the distal end of the device has been advanced at least partially into tissue at a desired site within the patient's body;

c. withdrawing the outer tubular member to expose the distal extremity of the probe;

d. applying a vacuum to the inner lumen of the probe to secure tissue to the distal extremity;

e. energizing the first electrode while distally advancing the first electrode over the distal extremity of the probe to separate a tissue specimen from the tissue site;

f. withdrawing the elongated probe member with the tissue specimen attached thereto from the patient leaving the outer tubular member in place with the distal end thereof at the tissue site;

g. advancing an elongated probe member as described in claim 15 through the outer tubular member to the tissue site and adjusting the relative positions of the probe and outer tubular member so as to expose the distal extremity of the probe member;

h. repeating steps d. and e. to obtain another tissue specimen; and i. after step h., withdrawing the probe member and specimen from the patient.

* * * * *